United States Patent
Gu et al.

(10) Patent No.: US 12,161,749 B2
(45) Date of Patent: Dec. 10, 2024

(54) MICRONEEDLE-ARRAY PATCHES WITH GLUCOSE-RESPONSIVE MATRIX FOR CLOSED-LOOP INSULIN DELIVERY

(71) Applicant: NORTH CAROLINA STATE UNIVERSITY, Raleigh, NC (US)

(72) Inventors: Zhen Gu, Los Angeles, CA (US); Jicheng Yu, Raleigh, NC (US); Guojun Chen, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 856 days.

(21) Appl. No.: 17/270,953

(22) PCT Filed: Aug. 26, 2019

(86) PCT No.: PCT/US2019/048063
§ 371 (c)(1),
(2) Date: Feb. 24, 2021

(87) PCT Pub. No.: WO2020/041787
PCT Pub. Date: Feb. 27, 2020

(65) Prior Publication Data
US 2021/0244658 A1   Aug. 12, 2021

Related U.S. Application Data

(60) Provisional application No. 62/727,290, filed on Sep. 5, 2018, provisional application No. 62/722,438, filed on Aug. 24, 2018.

(51) Int. Cl.
*A61K 9/00* (2006.01)
*A61M 37/00* (2006.01)
*C08F 220/34* (2006.01)

(52) U.S. Cl.
CPC ....... *A61K 9/0021* (2013.01); *A61M 37/0015* (2013.01); *C08F 220/34* (2013.01); *A61M 2037/0061* (2013.01)

(58) Field of Classification Search
CPC ...... A61M 37/0015; A61M 2037/0023; A61M 2037/003
See application file for complete search history.

(56) References Cited

U.S. PATENT DOCUMENTS 6,486,213 B1 * 11/2002 Chen .................. A61K 9/2027
525/78
2015/0057590 A1   2/2015 Center

FOREIGN PATENT DOCUMENTS

JP    H06192069 A    7/1994
WO   2018/085809 A1  5/2018
(Continued)

OTHER PUBLICATIONS

"Kitano et al., A novel drug delivery system utilizing a glucose responsive polymer complex between poly (vinyl alcohol) and poly (N-vinyl-2-pyrrolidone) with a phenylboronic acid moiety, Mar. 1992, Journal of Controlled Release, vol. 19, pp. 161-170" (Year: 1992).*

(Continued)

*Primary Examiner* — Dung T Ulsh
(74) *Attorney, Agent, or Firm* — Meunier Carlin & Curfman LLC

(57) ABSTRACT

Disclosed are compositions and methods for microneedle patches comprising copolymer designed for glucose triggered insulin delivery. In one aspect, disclosed herein are microneedle patches comprising insulin loaded copolymers; wherein the insulin dissociates from the microneedle in an hyperglycemic environment; wherein the copolymer comprises poly(N-vinylpyrrolidone-co-2-N(dimethylamino)

(Continued)

ethyl acrylate-co-3-(acrylamido)phenylboronic acid and methods of their use.

9 Claims, 8 Drawing Sheets

(56) References Cited

FOREIGN PATENT DOCUMENTS

| | | |
|---|---|---|
| WO | 2018106696 A1 | 6/2018 |
| WO | 2018/165294 A1 | 9/2018 |

OTHER PUBLICATIONS

"Zhang et al., Highly stable and degradable multifunctional microgel for self-regulated insulin delivery under physiological conditions , May 7, 2013, Nanoscale, vol. 5, pp. 6498-6506" (Year: 2013).*
Hardy, J.G., et al., "Hydrogel-Forming Microneedle Arrays Made from light-Responsive Materials for On-Demand Transdermal Drug Delivery," Molecular Pharmaceuticals, vol. 13, 2016, pp. 907-914.
Zhang, Y., et al., "Bioresponsive Microneedles with a Sheath Structure for H2O2 and pH Cascade-Triggered Insulin Delivery," Small, vol. 14, No. 14, 2018, 13 pages.
Extended European Search Report, dated Apr. 19, 2022, received in connection with corresponding EP Patent Application No. 19851324. 4.
Association, A. D., Standards of medical care in diabetes—2017 abridged for primary care providers. Clin. Diabetes 2017, 35 (1), 5-26.
Atkinson, M. A.; Eisenbarth, G. S., Type 1 diabetes: new perspectives on disease pathogenesis and treatment. Lancet 2001, 358 (9277), 221-229.
Bakh, A. B. Cortinas, M. A. Weiss, R. S. Langer, D. G. Anderson, Z. Gu, S. Dutta, M. S. Strano, Glucose-responsive insulin by molecular and physical design. Nat. Chem. 9, 937 (2017).
Bratlie, K. M.; York, R. L.; Invernale, M. A.; Langer, R.; Anderson, D. G., Materials for diabetes therapeutics. Adv Healthc Mater 2012, 1 (3), 267-84.
Brooks, W. L.; Sumerlin, B. S., Synthesis and applications of boronic acid-containing polymers: From materials to medicine. Chem. Rev. 2015, 116 (3), 1375-1397.
Brownlee, A. Cerami, A glucose-controlled insulin-delivery system: semisynthetic insulin bound to lectin. Science 206, 1190-1191 (1979).
Brownlee, M.; Cerami, A., Glycosylated insulin complexed to concanavalin A: biochemical basis for a closed-loop insulin delivery system. Diabetes 1983, 32 (6), 499-504.
Chou, D. H.-C.; Webber, M. J.; Tang, B. C.; Lin, A. B.; Thapa, L. S.; Deng, D.; Truong, J. V.; Cortinas, A. B.; Langer, R.; Anderson, D. G., Glucose-responsive insulin activity by covalent modification with aliphatic phenylboronic acid conjugates. Proc. Natl. Acad. Sci. U. S. A. 2015, 112 (8), 2401-2406.
Ding, Y. Guan, Y. Zhang, X. Zhu, Layer-by-layer multilayer films linked with reversible boronate ester bonds with glucose-sensitivity under physiological conditions. Soft Matt. 5, 2302-2309 (2009).
Fischel-Ghodsian, F.; Brown, L.; Mathiowitz, E.; Brandenburg, D.; Langer, R., Enzymatically controlled drug delivery. Proc. Natl. Acad. Sci. U. S. A. 1988, 85 (7), 2403-2406.
Gordijo, C. R.; Koulajian, K.; Shuhendler, A. J.; Bonifacio, L. D.; Huang, H. Y.; Chiang, S.; Ozin, G. A.; Giacca, A.; Wu, X. Y., Nanotechnology-enabled closed loop insulin delivery device: In vitro and in vivo evaluation of glucose-regulated insulin release for diabetes control. Adv. Funct. Mater. 2011, 21 (1), 73-82.
Gu, A. A. Aimetti, Q. Wang, T. T. Dang, Y. Zhang, O. Veiseh, H. Cheng, R. S. Langer, D. G. Anderson, Injectable nano-network for glucose-mediated insulin delivery. ACS Nano 7, 4194-4201 (2013).
Gu, Z.; Dang, T. T.; Ma, M.; Tang, B. C.; Cheng, H.; Jiang, S.; Dong, Y.; Zhang, Y.; Anderson, D. G., Glucose-responsive microgels integrated with enzyme nanocapsules for closed-loop insulin delivery. ACS Nano 2013, 7 (8), 6758-66.
Hisamitsu, K. Kataoka, T. Okano, Y. Sakurai, Glucose-responsive gel from phenylborate polymer and poly (vinyl alcohol): prompt response at physiological pH through the interaction of borate with amino group in the gel. Pharm. Res. 14, 289-293 (1997).
Ito, Y.; Casolaro, M.; Kono, K .; Imanishi, Y., An insulin-releasing system that is responsive to glucose. J. Controlled Release 1989, 10 (2), 195-203.
Kataoka, H. Miyazaki, M. Bunya, T. Okano, Y. Sakurai, Totally synthetic polymer gels responding to external glucose concentration: their preparation and application to on-off regulation of insulin release. J. Am. Chem. Soc. 120, 12694-12695 (1998).
Kost, K. Leong, R. Langer, Ultrasound-enhanced polymer degradation and release of incorporated substances. Proc. Natl. Acad. Sci. U. S. A. 86, 7663-7666 (1989).
Larsen, B. Rolin, Use of the Göttingen minipig as a model of diabetes, with special focus on type 1 diabetes research. ILAR journal 45, 303-313 (2004).
Larsen, M. Elander, J. Sturis, M. Wilken, R. Carr, B. Rolin, N. Pørksen, The conscious Göttingen minipig as a model for studying rapid pulsatile insulin secretion in vivo. Diabetologia 45, 1389-1396 (2002).
Lu, Y.; Aimetti, A. A.; Langer, R.; Gu, Z., Bioresponsive materials. Nat. Rev. Mater. 2016, 2, 16075.
Matsumoto, A.; Yoshida, R.; Kataoka, K., Glucose-responsive polymer gel bearing phenylborate derivative as a glucose-sensing moiety operating at the physiological pH. Biomacromolecules 2004, 5 (3), 1038-1045.
Matsumoto, M. Tanaka, H. Matsumoto, K. Ochi, Y. Moro-oka, H. Kuwata, H. Yamada, I. Shirakawa, T. Miyazawa, H. Ishii, Synthetic "smart gel" provides glucose-responsive insulin delivery in diabetic mice. Sci. Adv. 3, eaaq0723 (2017).
Matsumoto, T. Ishii, J. Nishida, H. Matsumoto, K. Kataoka, Y. Miyahara, A synthetic approach toward a self-regulated insulin delivery system. Angew. Chem. Int. Ed. 51, 2124-2128 (2012).
Mo, R.; Jiang, T.; Di, J.; Tai, W.; Gu, Z., Emerging micro-and nanotechnology based synthetic approaches for insulin delivery. Chem. Soc. Rev. 2014, 43 (10), 3595-3629.
Ohkubo, Y.; Kishikawa, H.; Araki, E.; Miyata, T.; Isami, S.; Motoyoshi, S.; Kojima, Y.; Furuyoshi, N.; Shichiri, M., Intensive insulin therapy prevents the progression of diabetic microvascular complications in Japanese patients with non-insulin-dependent diabetes mellitus: a randomized prospective 6-year study. Diabetes Res. Clin. Pract. 1995, 28 (2), 103-117.
Owens, D. R.; Zinman, B.; Bolli, G. B., Insulins today and beyond. Lancet 2001, 358 (9283), 739-746.
Peppas, N.; Huang, Y.; Torres-Lugo, M.; Ward, J.; Zhang, J., Physicochemical foundations and structural design of hydrogels in medicine and biology. Annu. Rev. Biomed. Eng. 2000, 2 (1), 9-29.
Podual, F. Doyle Iii, N. Peppas, Preparation and dynamic response of cationic copolymer hydrogels containing glucose oxidase. Polymer 41, 3975-3983 (2000).
Podual, K.; Doyle, F. J.; Peppas, N. A., Glucose-sensitivity of glucose oxidase-containing cationic copolymer hydrogels having poly (ethylene glycol) grafts. J. Controlled Release 2000, 67 (1), 9-17.
Prausnitz, Microneedles for transdermal drug delivery. Adv. Drug Del. Rev. 56, 581-587 (2004).
Prausnitz, R. Langer, Transdermal drug delivery. Nat. Biotechnol. 26, 1261 (2008).
Ravaine, C. Ancla, B. Catargi, Chemically controlled closed-loop insulin delivery. J. Controlled Release 132, 2-11 (2008).
Shiino, D.; Murata, Y.; Kubo, A.; Kim, Y. J.; Kataoka, K.; Koyama, Y.; Kikuchi, A.; Yokoyama, M.; Sakurai, Y.; Okano, T., Amine containing phenylboronic acid gel for glucose-responsive insulin release under physiological pH. J. Controlled Release 1995, 37 (3), 269-276.
Stumvoll, M.; Goldstein, B. J.; van Haeften, T. W., Type 2 diabetes: principles of pathogenesis and therapy. Lancet 2005, 365 (9467), 1333-1346.

(56) References Cited

OTHER PUBLICATIONS

Sullivan, N. Murthy, M. R. Prausnitz, Minimally invasive protein delivery with rapidly dissolving polymer microneedles. Adv. Mater. 20, 933-938 (2008).
Sullivan, S. P.; Koutsonanos, D. G.; del Pilar Martin, M.; Lee, J. W.; Zarnitsyn, V.; Choi, S. O.; Murthy, N.; Compans, R. W.; Skountzou, I.; Prausnitz, M. R., Dissolving polymer microneedle patches for influenza vaccination. Nat. Med. 2010, 16 (8), 915.
Summerfield, F. Meurens, M. E. Ricklin, The immunology of the porcine skin and its value as a model for human skin. Mol. Immunol. 66, 14-21 (2015).
Swindle, A. Makin, A. Herron, F. Clubb Jr, K. Frazier, Swine as models in biomedical research and toxicology testing. Vet. Pathol. 49, 344-356 (2012).
Vancoillie, et al., Synthesis and polymerization of boronic acid containing monomers. Polym. Chem. 7, 5484-5495 (2016).
Veiseh, O.; Tang, B. C.; Whitehead, K. A.; Anderson, D. G.; Langer, R., Managing diabetes with nanomedicine: challenges and opportunities. Nat. Rev. Drug Discov. 2015, 14 (1), 45-57.
Wang, C.; Ye, Y.; Sun, W.; Yu, J.; Wang, J.; Lawrence, D. S.; Buse, J. B.; Gu, Z., Red Blood Cells for Glucose-Responsive Insulin Delivery. Adv. Mater. 2017, 29 (18).
Wu, L. Wang, H. Yu, J. Wang, Z. Chen, Organization of glucose-responsive systems and their properties. Chem. Rev. 111, 7855-7875 (2011).
Wu, N. Mitra, E. C. Yan, S. Zhou, Multifunctional hybrid nanogel for integration of optical glucose sensing and self-regulated insulin release at physiological pH. ACS Nano 4, 4831-4839 (2010).
Wu, Z. Li, X.-X. Chen, J.S. Fossey, T. D. James, Y.-B. Jiang, Selective sensing of saccharides using simple boronic acids and their aggregates. Chem. Soc. Rev. 42, 8032-8048 (2013).
Yang, M. Wu, S. Lin, R. P. Nargund, X. Li, T. Kelly, L. Yan, G. Dai, Y. Qian, Q. Dallas-Yang, A glucose-responsive insulin therapy protects animals against hypoglycemia. JCI insight 3, (2018).
Ye, X. Jiang, W. Xu, M. Zhou, Y. Hu, W. Wu, Tailoring the glucose-responsive vol. phase transition behaviour of Ag@ poly (phenylboronic acid) hybrid microgels: from monotonous swelling to monotonous shrinking upon adding glucose at physiological pH. Polym. Chem.y 5, 2352-2362 (2014).
Yu, J.; Qian, C.; Zhang, Y.; Cui, Z.; Zhu, Y.; Shen, Q.; Ligler, F. S.; Buse, J. B.; Gu, Z., Hypoxia and H2O2 dual-sensitive vesicles for enhanced glucose-responsive insulin delivery. Nano Lett. 2017, 17 (2), 733-739.
Yu, J.; Zhang, Y.; Ye, Y.; DiSanto, R.; Sun, W.; Ranson, D.; Ligler, F. S.; Buse, J. B.; Gu, Z., Microneedle-array patches loaded with hypoxia-sensitive vesicles provide fast glucose-responsive insulin delivery. Proc. Natl. Acad. Sci. U. S. A. 2015, 112 (27), 8260-5.
Yu, Y. Zhang, A. R. Kahkoska, Z. Gu, Bioresponsive transcutaneous patches. Curr. Opin. Biotechnol. 48, 28-32 (2017).
Yu, Y. Zhang, H. Bomba, Z. Gu, Stimuli-responsive delivery of therapeutics for diabetes treatment. Bioeng. Transl. Med. 1, 323-337 (2016).
Zhang, J. Yu, A. R. Kahkoska, J. Wang, J. B. Buse, Z. Gu, Advances in transdermal insulin delivery. Adv. Drug Del. Rev., (2018).
International Search Report and Written Opinion issued in PCT/US2019/048063, dated Nov. 15, 2019, 9 pages.
Yang et al. "Recent Advances of Microneedles for Biomedical Applications: Drug Delivery and Beyond," Acta Pharmaceutica Sinica B, May 1, 2019 (May 1, 2019), vol. 9, Iss. 3, pp. 469-483.
English translation of Notice of Reasons for Refusal for Japanese Application No. 2021-509922 dated Jul. 4, 2023.
Zhang et al., Bioresponsive Microneedles with a Sheath Structure for H2O2 and pH Cascade-Triggered Insulin Delivery, Nano-Micro Small, vol. 14, No. 14, p. 1-7, Apr. 5, 2018.
English translation of Office Action for Chinese Application No. 201980068619.7 dated Sep. 1, 2023.
Kitano, et al., Effect of the Incorporation of Amino Groups in a Glucose-responsive Polymer Complex Having Phenylboronic Acid Moieties, Polymers for Advanced Technologies, vol. 2, pp. 261-264.
De Geest, et al., Glucose-Responsive Polyelectrolyte Capsules, American Chemical Society, vol. 22, No. 11, pp. 5070-5074.

\* cited by examiner

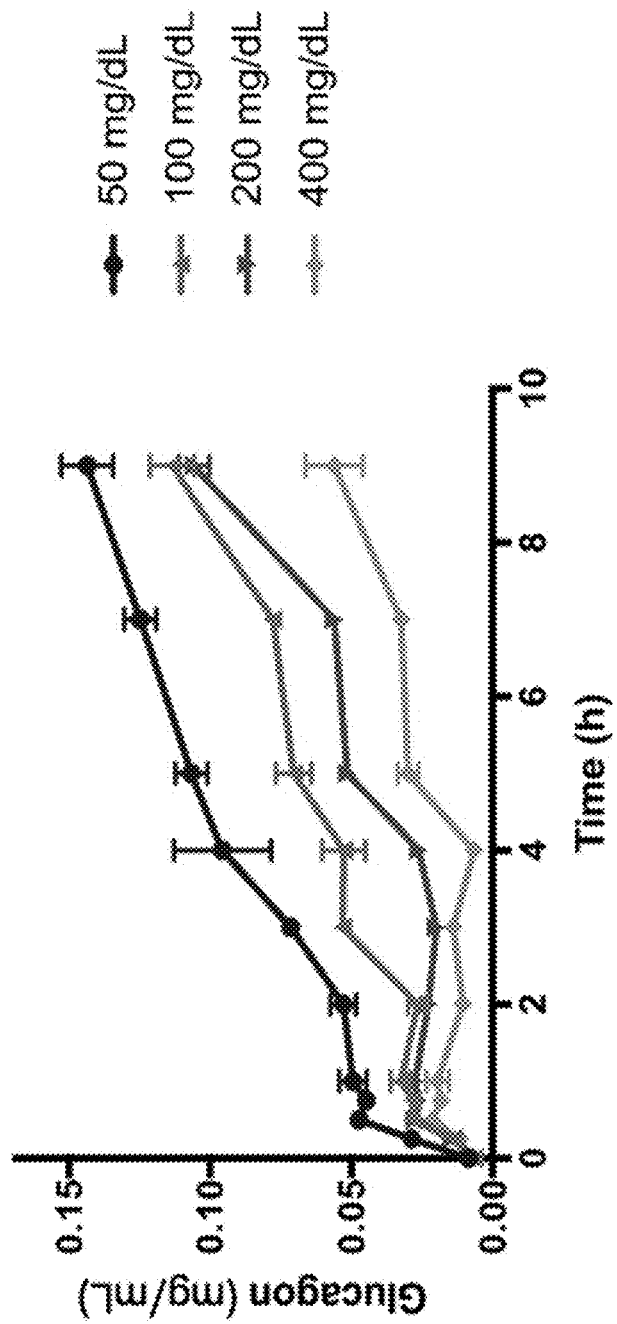
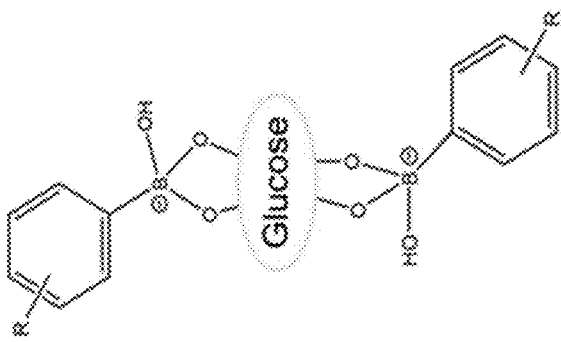
FIG. 8

MICRONEEDLE-ARRAY PATCHES WITH GLUCOSE-RESPONSIVE MATRIX FOR CLOSED-LOOP INSULIN DELIVERY

This application is a national stage application filed under 35 U.S.C. § 371 of PCT International Application No. PCT/US2019/048063, filed on Aug. 26, 2019, entitled "MICRONEEDLE-ARRAY PATCHES WITH GLUCOSE-RESPONSIVE MATRIX FOR CLOSED-LOOP INSULIN DELIVERY," which claims the benefit of U.S. Provisional Application No. 62/722,438, filed on Aug. 24, 2018 and U.S. Provisional Application No. 62/727,290, filed on Sep. 5, 2018, applications which are incorporated herein by reference in their entirety.

BACKGROUND

Diabetes currently affects 415 million people worldwide and this number is expected to increase to 642 million by 2040. Insulin is essential for survival in type 1 diabetes and often required for treatment of type 2 diabetes in order to control glycemia and prevent complications. However, traditional exogenous insulin administration, "open-loop subcutaneous injection" cannot match the exquisite regulation of blood glucose achieved by β-cells within the pancreatic islets of Langerhans, where endogenous insulin secretion is linked through metabolism to glucose transport. Poor glucose control results in a high risk for diabetes complications, such as limb amputation, blindness and kidney failure. In addition, hypoglycemia can lead to behavioral and cognitive disturbance, seizure, coma, brain damage, or death.

A closed-loop system that can "secret" desirable amounts of insulin in response to hyperglycemia while maintaining basal insulin release kinetics under normoglycemia is urgently needed. Electronic closed-loop devices that have been developed to this end remain challenges regarding algorithm accuracy and sensor reliability. Alternatively, chemically-engineered formulations or devices with the assistance of GOx, phenylboronic acid (PBA) and glucose binding protein (GBP) have attracted increasing attention. Nonetheless, tough challenges remain to demonstrate a formulation or device for smart insulin delivery that would combine desired features, including (i) rapid in vivo glucose-responsive behavior with a similar pharmacokinetics to pancreatic β-cells', (ii) sufficient insulin loading capacity for daily usage, (iii) small size and/or simple design for ease of administration, iv) feasible for large-scale manufacturing, and v) biocompatibility without acute and long-term toxicity. Therefore, there remains an ongoing need for the development of new smart insulin delivery systems not hindered by the deficiencies of present systems.

SUMMARY

Disclosed are methods and compositions related to microneedle patches for insulin delivery. For example, disclosed herein are microneedle patches comprising insulin loaded copolymers; wherein the insulin dissociates from the microneedle in an hyperglycemic environment.

In one aspect, disclosed herein are microneedle patches comprising insulin loaded copolymers; wherein the insulin dissociates from the microneedle in an hyperglycemic environment; wherein the copolymer comprises poly(N-vinylpyrrolidone-co-2-(dimethylamino)ethyl acrylate-co-3-(acrylamido)phenylboronic acid.

Also disclosed herein are microneedle patches of any preceding aspect, wherein the copolymers further comprises ethylene glycol dimethacrylate (EGDMA), and wherein the EGDMA is incorporated into the microneedle and crosslinks the insulin loaded polymers.

Also disclosed herein are self-regulating insulin delivery systems comprising the microneedle patch of any preceding aspect.

In one aspect, disclosed herein are methods of treating, reducing, inhibiting, or preventing hyperglycemia or a disease that comprises hyperglycemia as a symptom (including, but not limited to diabetes (type I or type II) in a subject comprising administering to the in a subject the microneedle patch or self-regulating insulin delivery systems of any preceding aspect. Thus, in one aspect, disclosed herein are method of treating, reducing, inhibiting, or preventing hyperglycemia or a disease that comprises hyperglycemia as a symptom (including, but not limited to diabetes (type I or type II) comprising administering to the subject a microneedle patch comprising insulin loaded copolymers; wherein the copolymers comprise N-vinylpyrrolidone (NVP), poly(vinyl alcohol) (PVA) or methacrylate PVA(m-PVA), 2-(dimethylamino)ethyl acrylate (DMAEA), 3-(acrylamido)phenylboronic acid (3APBA), ethylene glycol dimethacrylate (EGDMA), 2-(dimethylamino)ethyl methacrylate, and/or 4-(bromoethyl)phenylboronic acid (such as, for example, poly(N-vinylpyrrolidone-co-2-(dimethylamino)ethyl acrylate-co-3-(acrylamido)phenylboronic acid); wherein the copolymers further comprise insulin; and wherein the insulin dissociates from the microneedle in an hyperglycemic environment.

DESCRIPTION OF DRAWINGS

FIG. 1A shows a schematic of the fabrication process of smart insulin patch from a silicone mold using an in-situ photo-polymerization strategy. FIG. 1B shows the mechanism of glucose-triggered insulin release from GR-MNs. Under a hyperglycemic state, the increased negative charges by the formation of the glucose-boronate complexes can induce the volume phase transition of polymeric matrix and weaken the electrostatic interaction between negatively-charged insulin and polymers, promoting the quick release of insulin from the MNs. Blood glucose levels of diabetic pigs can be effectively regulated by the administration of smart insulin patch. FIG. 1C shows the characterization of GR-MN. (i) Representative photograph of the GR-MN patch. (ii) Representative SEM image of the MN array. Scale bar: 500 μm. (iii) Representative phase contrast (upper) and fluorescent microscopy (lower) of the rhodamine B-labeled insulin (red)-loaded MN patch. Scale bar: 500 μm.

FIG. 2A shows the mechanical behavior of the GR-MNs. FIG. 2B shows glucose-lowering activity of the insulin extracted from the fresh prepared patch in type 1 diabetic mice by comparing the initial BGLs and BGLs at 60 min post-injection of insulin solutions. Data are presented as mean ±S.D. (n=5). FIG. 2C shows glucose-lowering activity of the insulin extracted from the patches stored at room temperature. Data are presented as mean ±S.D. (n=5). FIG. 2D shows the glucose concentration-dependent glucose-binding capability. Data are presented as mean ±S.D. (n=5). FIG. 2E shows in vitro accumulated insulin release in several glucose concentrations at 37° C. Data are presented as mean ±S.D. (n=5). FIG. 2F shows pulsatile release profile presents the rate of insulin release as a function of glucose concentration (blue: 100 mg/dL; red: 400 mg/dL). wer) of the rhodamine B-labeled insulin (red)-loaded MN patch. Scale bar: 500 μm.

FIG. 5A shows mouse dorsum skin (the area within blue dashed line) transcutaneously treated with MN patch. FIGS. 5B and 5C BGLs (5B) and plasma human insulin concentrations (5C) in STZ-induced diabetic mice after treatment with PBS solution, CR-MN, and GR-MN. Insulin dose: 0.5 mg. P<0.01, *P<0.001 for administration with GR-MN compared with CR-MN. Data are presented as mean±S.D. (n=5). FIG. 5D shows in vivo intraperitoneal glucose tolerance test in diabetic mice at 4 h post-administration of GR-MN or CR-MN in comparison with the healthy control mice. Glucose dose: 1.5 g/kg. P<0.01, *P<0.001 for administration with GR-MN compared with CR-MN. Data are presented as mean ±S.D. (n=5). FIG. 5E shows the responsiveness was calculated based on the area under the curve in 120 min, with the baseline set at the 0-min blood glucose reading. Data are presented as mean ±S.D. (n=5). ***P<0.001. Student's t test. FIG. 5F shows the in vivo glucose-responsive insulin release promoted by intraperitoneal glucose challenge at 4 h post-administration of GR-MN. Glucose dose: 3 g/kg. Data are presented as mean ±S.D. (n=5). The blue arrows indicate the timepoints of MN administration in (5B-5C), and the red arrows indicate the timepoints of glucose administration in (5D) and (5F).

FIG. 6A shows a schematic of the minipig with CGMS treated with GR-MN at the leg site (top). Photograph of GR-MN applied on pig leg (bottom left). H&E stained section of minipig skin penetrated by one MN (bottom right). Scale bar: 200 μm. FIGS. 6B and 6C shows that BGLs in three STZ-induced diabetic minipigs after treatment with GR-MN (6B) and CR-MN (6C), respectively. Insulin dose: 7 mg. FIG. 6D shows an in vivo oral glucose tolerance test in diabetic minipigs at 4 h post-administration of GR-MN or CR-MN. Glucose dose: 1 g/kg. Data are presented as mean ±S.D. (n=3). FIG. 6E shows the responsiveness was calculated based on the area under the curve in 150 min, with the baseline set at the 0-min blood glucose reading. Data are presented as mean ±S.D. (n=3). **P<0.01, Student's t test. FIG. 6F shows the in vivo glucose-responsive insulin release promoted by intravenous glucose challenge at 4 h post-administration of GR-MN. Glucose dose: 0.7 g/kg. Data are presented as mean ±S.D. (n=3). The blue arrows indicate the timepoints of MN administration, and the pink arrows indicate the timepoints of feeding in (6B-6C). The red arrows indicate the timepoints of glucose administration in (6D) and (6F).

FIG. 8 shows a schematic of bis-complexation formed by one glucose molecule with two PBA molecules (Left). In vitro glucose-responsive release of glucagon in pH 7.4 phosphate buffer supplemented with glucose mimicking hyperglycemia (200 mg/dL, 400 mg/dL), normoglycemia (100 mg/dL), or hypoglycemia (50 mg/dL). Data are presented as mean ±S.D. (n=3) (Right).

DETAILED DESCRIPTION

Figure 1:
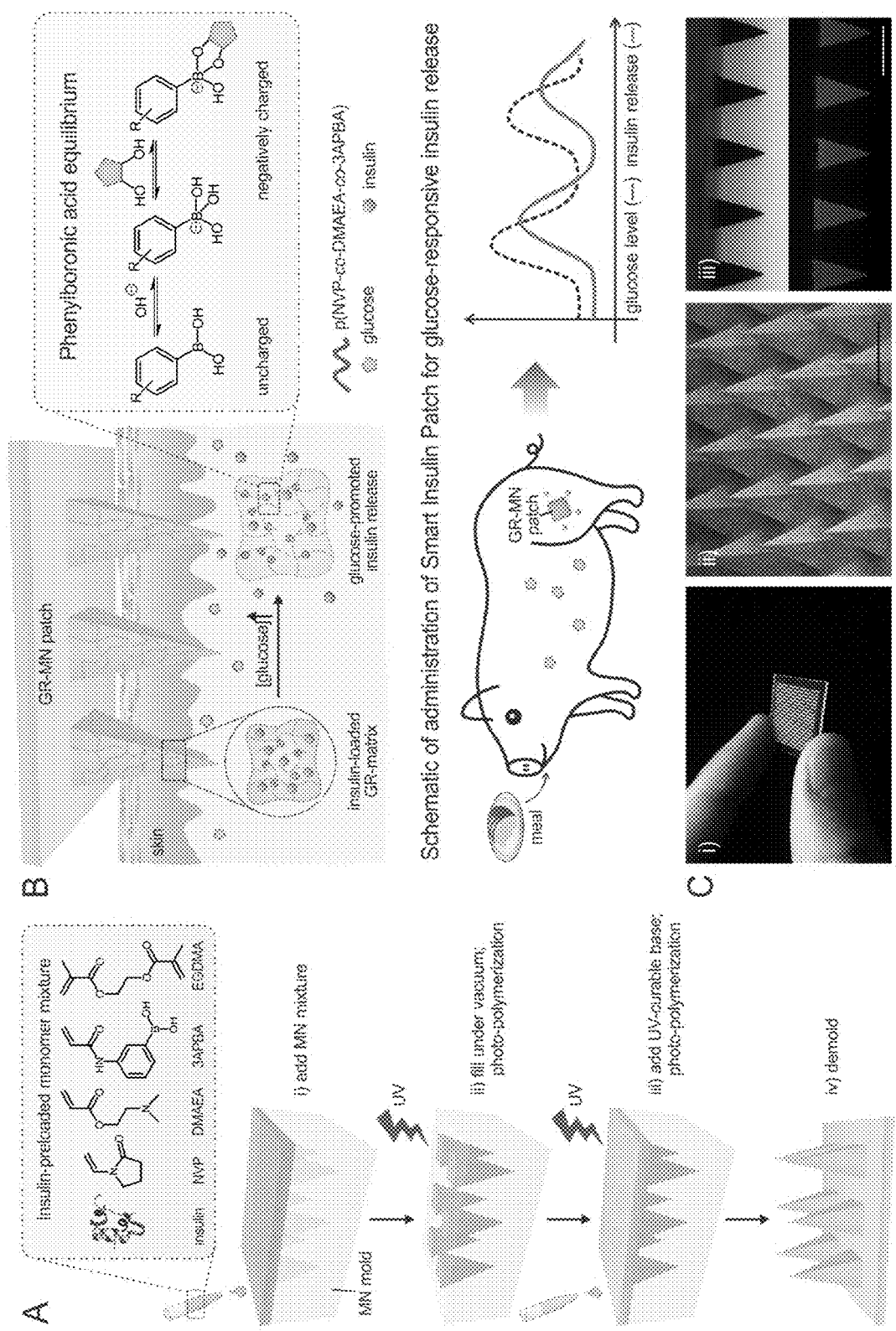
FIGS. 1A, 1B, and 1C shows a schematic of the glucose-responsive insulin delivery system using MNs-array patches with glucose-responsive matrix (GR-matrix).

Disclosed herein is a composition and method for treating, reducing, inhibiting, or preventing hyperglycemia including, but not limited to disease such as diabetes (Type I or Type II) that comprise as a symptom hyperglycemia. The composition includes an insulin molecule. In some embodiments, the composition further comprises a bioactive derivative of insulin. Suitable non-insulin-based treatment agents for use in the treatment of diabetes include, but are not limited to, insulin sensitizers, DPP IV inhibitors, glucagon-like peptide 1 (GLP-1) and analogs thereof, insulin secretagogues, such as, but not limited to sulfonylureas, meglitinides, gastric inhibitory polypeptide (GIP), insulin receptor activators, biguanides, thiazolidinediones, alpha-glucosidase inhibitors, and the like. The glucose responsive microneedles are configured to reversibly bind the insulin molecule, releasing the insulin in high glucose conditions. The method of treating diabetes includes administering the composition including the insulin molecule. In some embodiments, a pharmaceutically effective amount of the composition is administered to a subject having diabetes.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques.

"Biocompatible" generally refers to a material and any metabolites or degradation products thereof that are generally non-toxic to the recipient and do not cause any significant adverse effects to the subject.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

As used herein, "conjugated" refers to a non-reversible binding interaction.

As used herein, "displace" refers to interrupting a molecular or chemical interaction between, for example, a protein domain and a peptide, a protein domain and a chemical, a protein domain and a nucleic acid sequence by a chemical, peptide, or nucleic acid having affinity for that specific protein domain than the peptide, chemical, or nucleic acid being displaced.

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

An "effective amount" is an amount sufficient to effect beneficial or desired results. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, the term "high glucose conditions" refers to an environment having a glucose concentration greater than or equal to 200 mg/dL. For example, "high blood glucose levels" refer to glucose levels in the blood stream greater than or equal to 200 mg/dL. In some embodiments, high glucose conditions are 200-400 mg/dL. In other embodiments, high glucose conditions are 300-400 mg/dL.

A "linker" as used herein refers to a molecule that joins adjacent molecules. Generally a linker has no specific biological activity other than to join the adjacent molecules or to preserve some minimum distance or other spatial relationship between them. In some cases, the linker can be selected to influence or stabilize some property of the adjacent molecules, such as the folding, net charge, or hydrophobicity of the molecule.

As used herein, the term "low glucose conditions" refers to an environment having a glucose concentration from 0 to 200 mg/dL. For example, "low blood glucose levels" refer to glucose levels in the blood stream less than 200 mg/dL.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Pharmacologically active" active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., Type 1 diabetes). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired response is the control of type II diabetes. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. In some instances, the terms "treat", "treating," "treatment" and grammatical variations thereof, include controlling blood sugar levels and reducing the severity of diabetes symptoms as compared with prior to treatment of the subject or as compared with the incidence of such symptom in a general or study population.

1. A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

2. "Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

3. By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

4. By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "specifically binds," as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

Here, a new glucose-responsive microneedle (MN) array patch for self-regulated insulin delivery is described. Specifically, a new strategy was developed utilizing PBA as the glucose-responsive moiety to achieve on-demand microneedle (MN)-mediated transdermal insulin delivery. PBA can reversibly interact with glucose to generate cyclic boronate esters, which shifts the equilibrium from the uncharged group to the negatively charged one (FIG. 1a). It is understood and herein contemplated that other glucose-responsive moieties can be also included. For example, all native or synthetic glucose-binding molecules and proteins, and glucose oxidase (GOx)-loaded microneedles formed with pH, H2O2, or oxygen-sensitive polymers.

In one aspect, the glucose-responsive (GR) microneedle (MN) patch (GR MN) is made of the polymers of monomers of N-vinylpyrrolidone (NVP), poly(vinyl alcohol) (PVA) or methacrylate PVA(m-PVA), 2-(dimethylamino)ethyl acrylate (DMAEA), 3-(acrylamido)phenylboronic acid (3APBA), ethylene glycol dimethacrylate (EGDMA), 2-(dimethylamino)ethyl methacrylate, and/or 4-(bromoethyl) phenylboronic acid.

It is understood and herein contemplated that disclosed glucose-responsive polymeric matrix used in the microneedles can be comprised of three different kinds of monomers, a) a monomer with glucose-responsive group; b) a monomer with positively charged group; c) a major monomer used to form the backbone of the matrix. In one aspect, the microneedles can comprise monomer with one vinyl group and one glucose-responsive group can be used. The glucose-responsive group can be a boronate group. Boronate sensors that bind glucose under physiological conditions are preferred. Examples of useful boronates include, but are not limited to, aryl boronates, aminomethyl-aryl-2-boronates, and other boronates with amino groups in the vicinity or aryl boronates substituted with electron-withdrawing groups for example, sulfo-, carboxy-, nitro-, cyano-, fluoro-phenyl boronates, pyridine boronates, pyridinium boronates or their combinations. In one example, a 3-(acrylamido)phenylboronic acid (3APBA) was used. The polymers making the microneedles can also comprise monomers with one vinyl group and one positively charged group can be used. Examples of useful positively charged groups include, but are not limited to, amino group, secondary amine group, tertiary amine group, quaternary ammonium group, and imidazolium. In one example, a 2-(dimethylamino)ethyl acrylate (DMAEA) was used. Furthermore, monomers with at least one vinyl group can be used to from the backbone of the matrix. Liquid monomer is preferred. Examples of useful monomer include, but are not limited to, heteroaromatic vinyls, acrylic esters, methacrylic esters, vinyl esters, allyl esters, mono-functional oxyacetylene-containing (meth)acrylates such as poly(ethylene glycol) ethyl ether methacrylate. It should be understood that one or more types of olefinic monomers can be used to make the matrix of the present invention. Depending on the end use, one can choose the desired combination of monomers and the desired type and amount of functionalization. In one example, a N-vinylpyrrolidone (NVP) was used. Thus, in one aspect, the polymers can be copolymers (including diblock copolymers) such as, for example, poly(N-vinylpyrrolidone-co-2-(dimethylamino)ethyl acrylate-co-3-(acrylamido)phenylboronic acid) [p(NVP-co-DMAEA-co-3APBA)], $mPEG_n$-poly(2-(dimethylamino)ethyl methacrylate-4-(bromoethyl)phenylboronic acid)$_{n1}$ ($MPEG_n$-P(DMAEMA-PBA)$_{n1}$); wherein n, represents the number of MPEG repeats and can any number of repeats be between about 1 and about 8,000 repeats, preferably, between about 2K and about 6K repeats, most preferably, between about 4.5K and about 5.5K repeats (for example 1, 2,3, 4, 5, 6, 7, 8, 9, 10, 10, 30, 40, 50, 60, 70, 80, 90, 100, 200, 300, 400, 500, 600, 700, 800, 900, 1K, 1.1K, 1.2K, 1.3K, 1.4K, 1.5K, 2K, 2.5K, 3K, 3.5K, 4K, 4.5K, 4.6K, 4.7K, 4.8K, 4.9K, 5K, 5.1K, 5.2K, 5.3K, 5.4K, 5.5K, 6K, 6.5K, 7K, 7.5K, or 8K; and wherein n1 represents the number of P(DMAEMA-PBA) repeats can any number of repeats be between about 1 and about 18,000 preferably, between about 4K and about 16K repeats, most preferably between about 6K and about 14K repeats (for example 1, 2,3, 4, 5, 6, 7, 8, 9, 10, 10, 30, 40, 50, 60, 70, 80, 90, 100, 200, 300, 400, 500, 600, 700, 800, 900, 1K, 1.1K, 1.2K, 1.3K, 1.4K, 1.5K, 2K, 2.5K, 3K, 3.5K, 4K, 4.5K, 4.6K, 4.7K, 4.8K, 4.9K, 5K, 5.1K, 5.2K, 5.3K, 5.4K, 5.5K, 6K, 6.5K, 7K, 7.5K, 8K, 8.5K, 9K, 9.5K, 10K, 10.5K, 11K, 11.5K, 12K, 12.5K, 13K, 13.5K, 14K, 14.5K, 15K, 15.5K, 16K, 16.5K, 17K, 17.5K, or 18K. For example, disclosed herein are microneedle patches comprising micelles comprising insulin and/or a glucose responsive enzyme, wherein the micelle comprises $MPEG_{5K}$-P(DMAEMA-PBA)$_{14K}$ or $MPEG_{5K}$-P(DMAEMA-PBA)$_{6K}$.

In one aspect, EGDMA can be used as a crosslinker such as for example, a p(NVP-co-DMAEA-co-3APBA) with an EGDMA crosslinker (FIG. 1b). Other crosslinking agents that can be used in the disclosed microneedle patches include crosslinking agents with at least two vinyl groups can be used to crosslink the polymeric matrix. Examples of useful crosslinker include, but are not limited to, ethylene glycol dimethacrylate, methylene bisacrylamide, Poly(ethylene glycol) diacrylate. In one example, an ethylene glycol dimethacrylate was used.

Briefly, when exposed to a hyperglycemic condition, the increase of charges within polymeric matrix due to the formation of a glucose-boronate complex in 3-APBA units leads to the swelling of MN, triggering a rapid diffusion of preloaded insulin into skin tissue. Under a normoglycemic condition, the inhibited volume phase transition decreases the insulin release rates, reducing the risk of hypoglycemia.

To stabilize the microneedles polymers, the microneedles can comprise a poly(vinyl alcohol) (PVA), EGDMA, or methacrylate PVA(m-PVA). The stabilization occurs via cross-linking via acid-inert ester bonds between the phenylboronic acids of P(DMAEMA-PBA) and cis-1,3-diols on PVA or N-vinylpyrolidone (NVP). In one aspect, the cross-linking of the micelles incapsulating insulin can be degradable. The crosslinking of m-PVA in the microneedles incorporating the preloaded insulin can form non-cleavable covalent bonds.

The disclosed microneedles release insulin under hyperglycemic conditions. It is understood and herein contemplated that under a hyperglycemic condition, the increase of charges within polymeric matrix due to the formation of a glucose-boronate complex in 3-APBA units leads to the swelling of MN, triggering a rapid diffusion of preloaded insulin into skin tissue. Under a normoglycemic condition, the inhibited volume phase transition decreases the insulin release rates, reducing the risk of hypoglycemia. In one aspect, a therapeutically effective amount of insulin continues to be released for at least 24, 36, 48, 60, 72, 96 hours.

In one aspect, the disclosed microneedle patches can comprise a plurality of microneedles, wherein the plurality of microneedles have a center-to-center interval of about 200 μm to about 800 μm, for example a center to center interval of about 200, 225, 250, 275, 300, 325, 350, 375, 400, 425, 450, 475, 500, 525, 550, 575, 600, 625, 650, 675, 700, 725, 750, 775, or 800 μm.

It is also understood and herein contemplated that the disclosed plurality of microneedles in the microneedle patches is effective when the length of the needle is sufficiently long to reach desired tissues below the dermal layer. Thus, in one aspect, disclosed herein are devices wherein the plurality of microneedles have a height of about 600 nm to 1.8 μm. For example, the plurality of microneedles can have a height of about 600, 650, 700, 750, 800, 850, 900, 950 nm, 1.0, 1.1, 1.2, 1.3, 1.4, 1.5, 1.6, 1.7, or 1.8 μm.

In one aspect, the disclosed microneedle patches can be a component of a self-regulating insulin delivery system.

The disclosed microneedle patches can provide self-regulating administration of insulin to a subject in need thereof. Thus, in one aspect, disclosed herein are methods of treating, reducing, inhibiting, or preventing hyperglycemia (such as, for example, hyperglycemia in a diabetic subject) in a subject comprising administering to the subject the microneedle patch of any preceding aspect. Thus, for example, disclosed herein are methods of treating, reducing, inhibiting, or preventing diabetes (such as Type I or Type II diabetes) in a subject comprising administering to the subject a glucose responsive microneedle patch comprising any of the copolymers (for example p(NVP-co-DMAEA-co-3APBA) disclosed herein); and wherein the insulin dissociates from the microneedle in an acidic, hyperglycemic, and/or oxidative environment.

As used herein, "Type I diabetes" refers to the form of diabetes mellitus resulting from the autoimmune destruction of insulin-producing cells and reduction of the body's ability to produce insulin. The loss of insulin results in increased blood sugar.

EXAMPLES

Diabetes, a chronic disease that often leads to severe secondary complications, afflicts over 425 million people globally nowa-days. Frequent monitoring of glucose levels and injection of in-sulin is the traditional method for people with type 1 and advanced type 2 diabetes, which is known as an open-loop system. However, this open-loop strategy is beyond satisfaction or even lethal when overdosing. A closed-loop system, in which monitoring and de-livery can occur without the patient's involvement, is able to re-lease insulin in response to elevated glucose concentrations and tightly regulate blood glucose levels within a normal range without the risk of hypoglycemia. Thus, a glucose-responsive insulin de-livery system that can intelligently mimic the function of pancreatic β-cells is considered a preferred solution to diabetes treatment.

To this end, a variety of glucose-responsive insulin delivery systems based on glucose oxidase (GOx), phenylboronic acid (PBA), and glucose-binding proteins as the glucose-monitoring moieties have been investigated. However, these methods are often limited by several challenges, including low insulin loading efficiency and content, slow response rates, intricate administration processes and potential biocompatibility issue.

Preparation and Characterization of Smart Insulin Patch.

The needles of the GR-MN patch were comprised of insulin-loaded glucose-responsive polymeric matrix, which is fabricated from insulin-preloaded monomer mixture of NVP, DMAEA, 3APBA, and EGDMA by in-situ photo-polymerization at 4° C. The NVP is chosen as the major monomer since it is liquid at ambient conditions, and can therefore act as the solvent to dissolve other monomers. The resulting MNs were arranged in a 20×20 array with each needle of pyramidal shape with a 400 μm sides at the base and a height of 900 μm. Afterwards, the base of the patch was further prepared using a flexible commercial UV-curable material. The fluorescence image of the GR-MN patch revealed rhodamine B-labelled insulin was uniformly distributed in the tip region of each needle (FIG. 1C). In addition, the in-situ photo-polymerization method led nearly to a 100% encapsulation efficiency of insulin with a high loading capability of 20 wt % for MNs, the target for potential clinical usage. It was further determined the fracture force of the MN was 0.75 N/needle using a tensile compression machine (FIG. 2A), which is sufficient for skin penetration without breaking.

Figure 2:
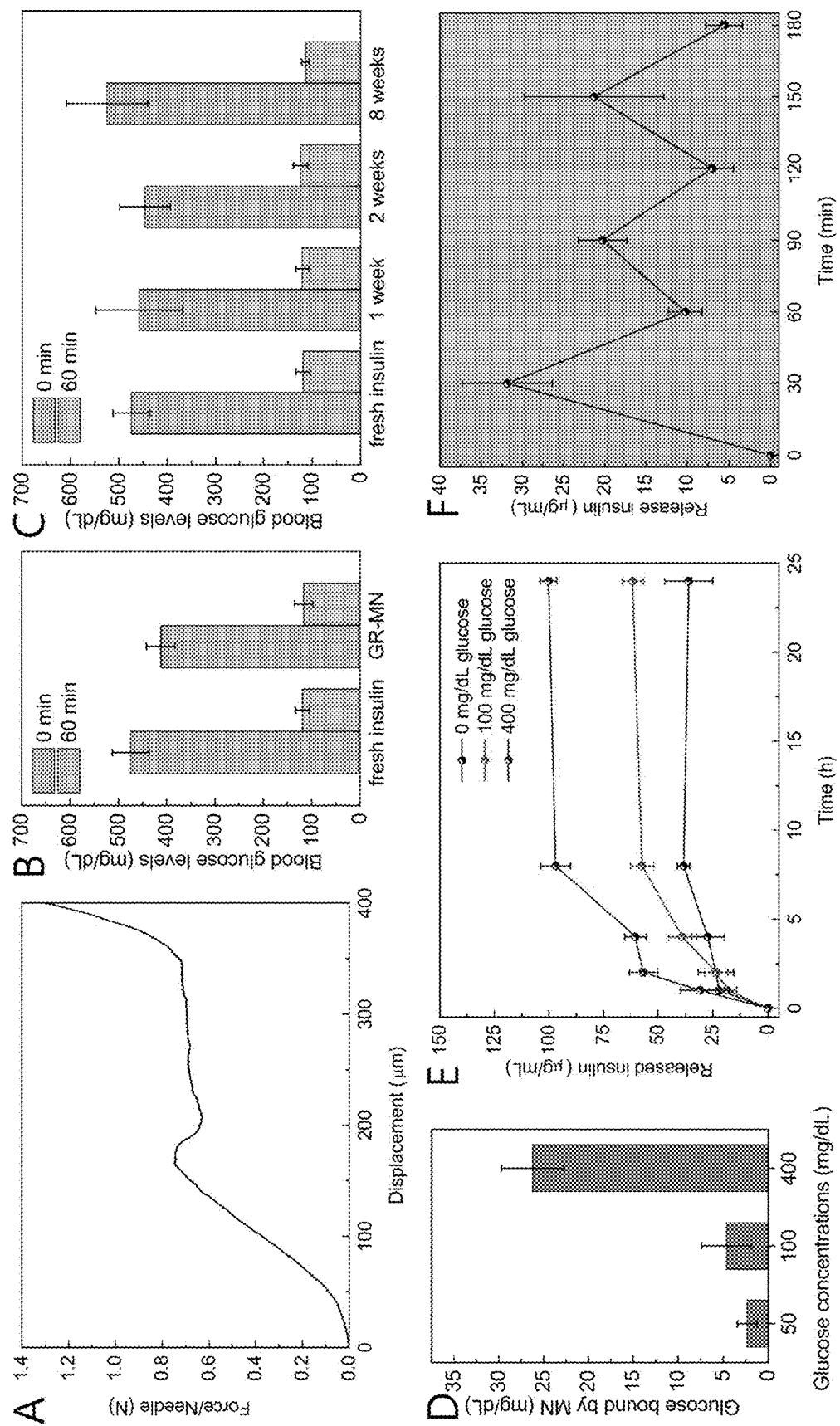
FIGS. 2A, 2B, 2C, 2D, 2E, and 2F shows the in vitro characterization of GR-MN.

During the fabrication of MN patches, avoidance of organic solvent and elevated temperature is required to maintain the stability of insulin. The insulin extracted from the resulting patches exhibited similar hypoglycemic effect as fresh insulin in diabetic mice (FIG. 2B). In addition, the polymeric MN can prevent denaturation of the loaded insulin at room temperature. By comparing the extracted insulin from the patches stored at room temperature to the fresh insulin solution, it was estimated that the stability of insulin within the patch can be maintained at room temperature for at least 8 weeks (FIG. 2C).

In Vitro Glucose-Responsive Insulin Release.

The PBA group has been used previously for the detection of glucose. An essential parameter for its selective binding to glucose is the pKa of the PBA group. In order to decrease the pKa of 3APBA to enhance its glucose recognition capability at physiological pH, the Lewis base DMAEA was introduced to stabilize the borate ester by electrostatic attraction (B--N+) through the protonated dimethyl amino groups. The glucose binding capability of the resulting 3APBA/DMAEA-contained polymeric matrix was measured by incubation in PBS buffer with varied glucose concentrations. The quantity of bound glucose by the polymeric matrix in a typical hyperglycemic state (400 mg/dL) was 5.7-fold greater than that bound in a normoglycemic state (100 mg/dL) (FIG. 2D).

Figure 3:
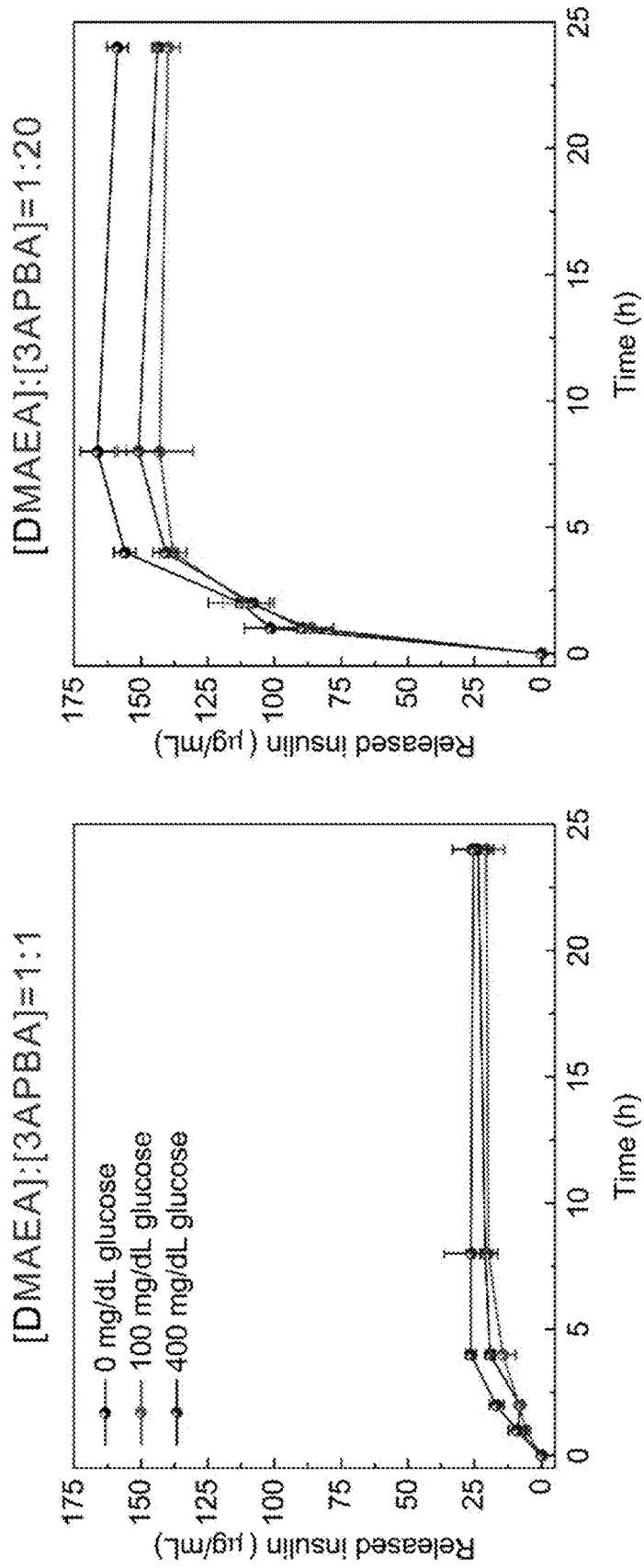
FIG. 3 shows the in vitro accumulated insulin release from the polymeric matrix with a ratio of DMAEA to 3APBA at a 1:1 ratio (left) or a 1:20 ratio (right) across different glucose concentrations at 37° C. Data are presented as mean ±S.D. (n=3).
Figure 4:
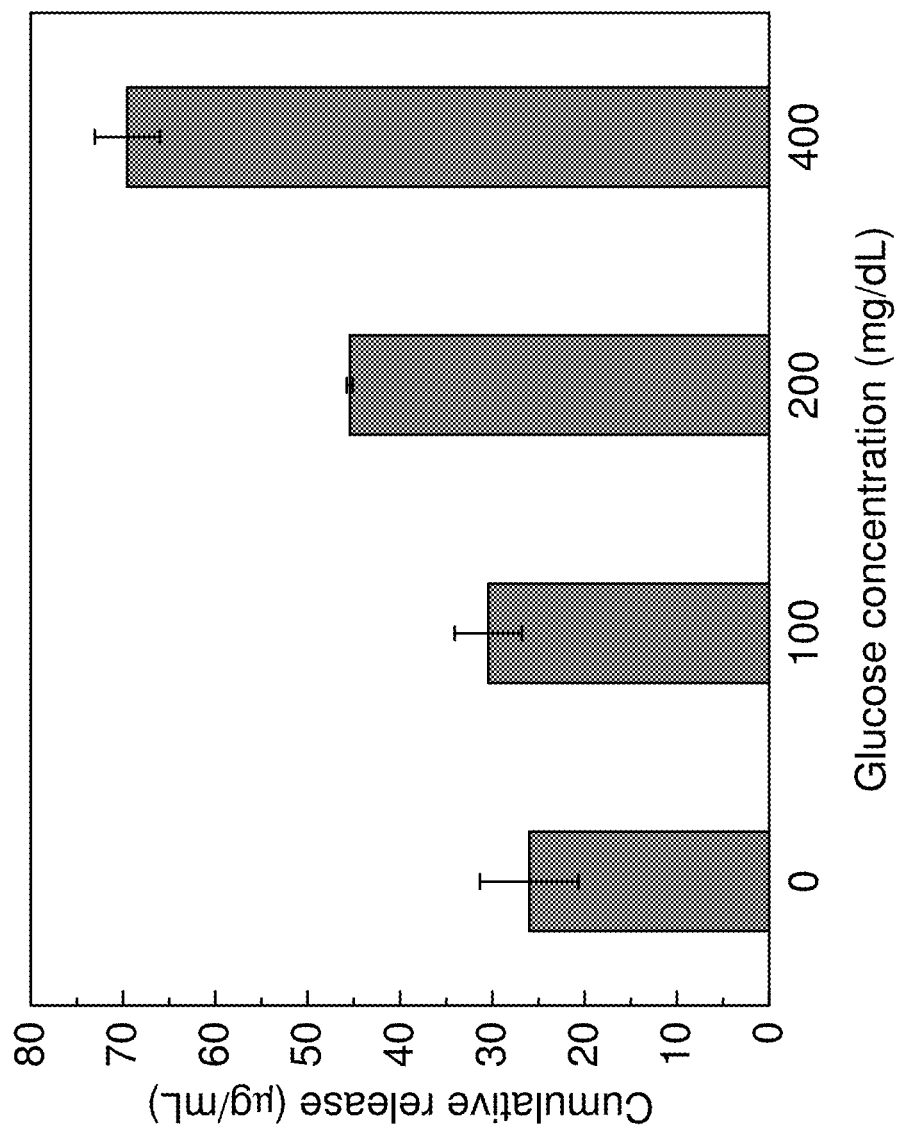
FIG. 4 shows the insulin release of the polymeric matrix with a 1:4 ratio of DMAEA to 3APBA at 1:4 as a function of glucose concentrations. Data are presented as mean ±S.D. (n=3).

The enhanced glucose-binding in hyperglycemic conditions leads to an increased density of negative charges within the polymeric matrix, causing the volume phase transition and weakening the electrostatic interaction between insulin and matrix. The release rates of insulin were studied across samples with different ratios of positively-charged units (DMAEA) to negatively-charged units (3APBA). As shown in FIG. 2E, in the polymeric matrix with a 1:4 ratio of DMAEA to 3APBA, a quick release of insulin was observed at the 400 mg/dL glucose level with a relatively slow release at the 0 or 100 mg/dL glucose level. By contrast, the release rates of insulin across all glucose concentrations were slow in the samples with a 1:1 ratio of DMAEA to 3APBA and the release rates were fast in the samples with a 1:20 ratio of DMAEA to 3APBA, which can be attributed to the excess positive or negative charges within the matrix (FIG. 3). Therefore, the polymeric matrix with a 1:4 ratio of DMAEA to 3APBA was used in all subsequent in vitro and in vivo studies. In addition, at the 1:4 ratio of DMAEA to 3ABPA, the rate of insulin release increased as glucose concentrations were gradually increased from normoglycemic to hyperglycemic conditions (FIG. 4). A pulsatile release profile of insulin was also achieved for several cycles by incubating in the normal and hyperglycemic solutions alternatively (FIG. 2F). Taken together, the results substantiate that the release rate of insulin from the polymeric matrix was regulated in a glucose-dependent manner.

In Vivo Studies of Smart Insulin Patch in a Type 1 Diabetic Mouse Model.

Figure 5:
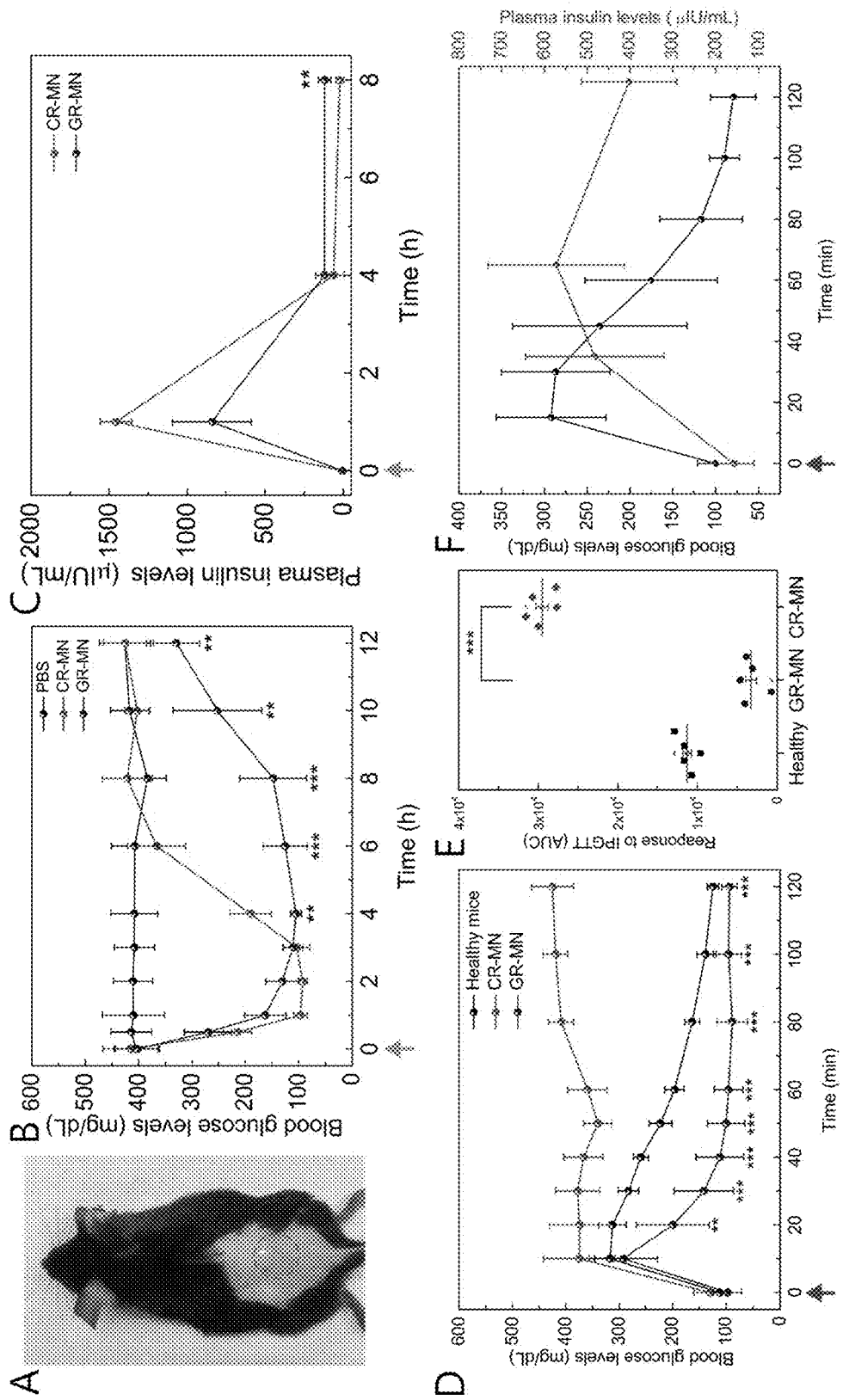
FIGS. 5A, 5B, 5C, 5D, 5E, and 5F show the in vivo evaluation of GR-MN in a type 1 diabetic mouse model.

The in vivo performance of the GR-MN was assessed in a streptozotocin (STZ)-induced type 1 diabetic mouse model. The diabetic mice were randomly grouped and transcutaneously exposed to different samples, including GR-MN and the non-responsive crosslinked MN (CR-MN) patches as a control (insulin dose: 0.5 mg) (FIG. 5A). The BGLs of treated mice were monitored over time. As expected, the BGLs in mice treated with CR-MN and GR-MN all decreased to below 200 mg/dL (FIG. 5B). However, the normoglycemic state could not be maintained in the groups treated with CR-MN, and the BGLs returned to a hyperglycemic state after 4 h. In contrast, the GR-MN was shown to regulate BGLs within the target range (<200 mg/dL) for more than 10 h presumably, owing to the smart glucose responsiveness. Plasma insulin measurement by enzyme-linked immunosorbent assay (ELISA) displayed the higher continuous insulin release in the GR-MN group, consistent with sustained euglycemic BGL levels (FIG. 5C).

Next, an intraperitoneal glucose tolerance test (IPGTT) was performed with a glucose dose of 1.5 g/kg at 4 h post-administration to assess blood glucose regulation capacity. As demonstrated in FIGS. 5D and 5E, the BGLs in healthy mice and diabetic mice treated with GR-MN returned to normoglycemia after a blood glucose peak, while the mice treated with CR-MN showed a gradual increase in BGLs over 120 min. To confirm the blood glucose-promoted insulin release in vivo, a glucose challenge with a higher dose (3 g/kg) was conducted in diabetic mice at 4 h post-administration of the GR-MN. An obvious spike in the plasma insulin levels was observed following the increased BGLs, after which BGLs gradually decreased, indicating the rapid glucose-responsiveness of the GR-MN (FIG. 5F). The hematoxylin and eosin (H&E) staining results showed insignificant neutrophil infiltration at the GR-MN-treated site after 1 week.

In Vivo Studies of Smart Insulin Patch in a Type 1 Diabetic Minipig Model.

Figure 6:
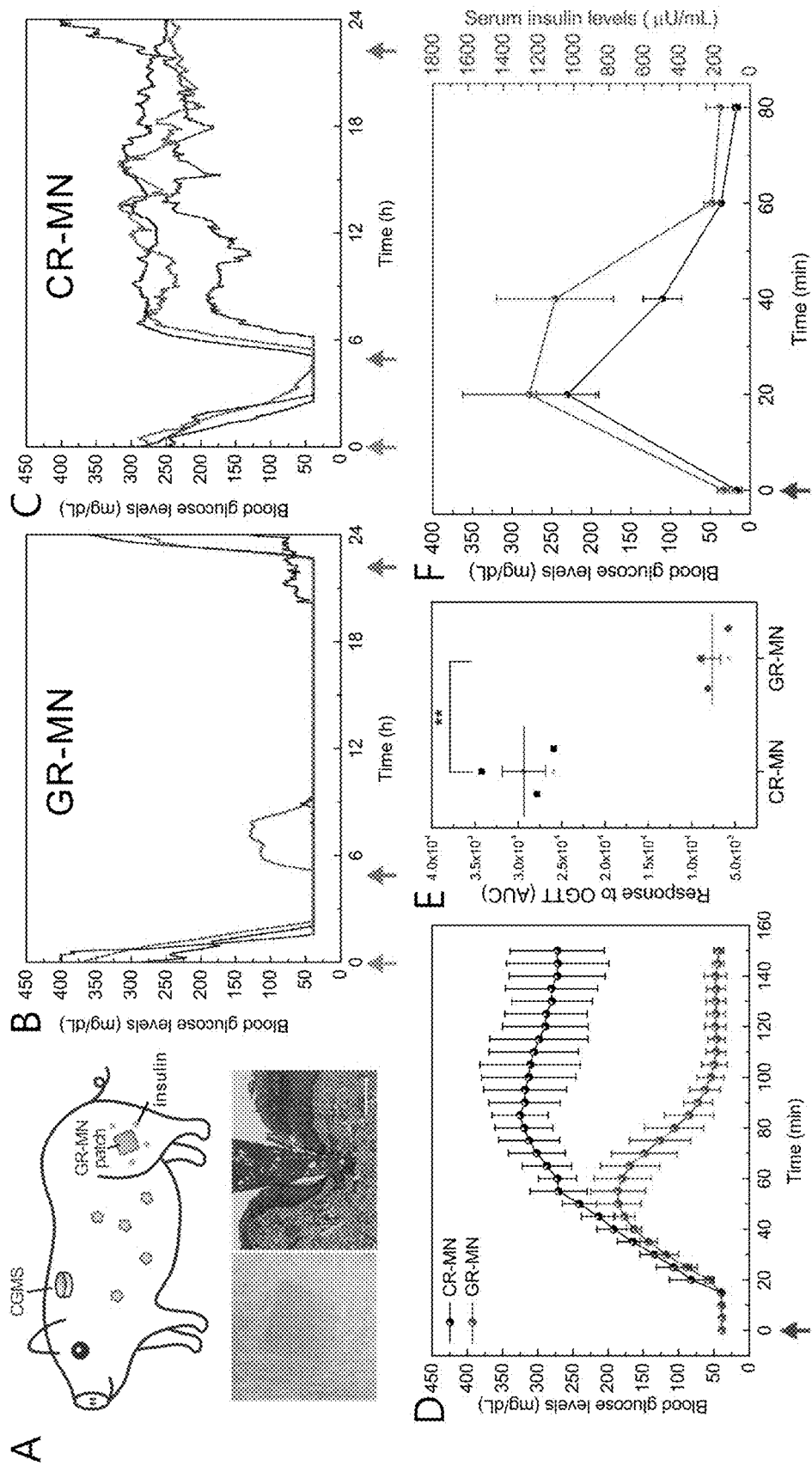
FIGS. 6A, 6B, 6C, 6D, 6E, and 6F show the in vivo evaluation of GR-MN in a type 1 diabetic minipig model.

Compared to a rodent model, glucose metabolism of the minipig is more analogous to the human system. In addition, the porcine skin has been considered as a good model for human skin in term of general structure, thickness, hair sparseness, collagen and lipid composition. Therefore the in vivo performance of the GR-MN was evaluated in a STZ-induced type 1 Gottingen minipig model. The diabetic minipigs were transcutaneously treated with CR-MN or GR-MN with an insulin dose of 7 mg under anesthesia, and then normally fed with 2 meals daily. As shown in FIG. 6A, the MN patch can effectively penetrate the skin of the minipig. In order to achieve real-time and sustained record of the minipig BGLs, a continuous glucose monitoring system (CGMS, Dexcom, U.S.A) was integrated in the minipigs experiments. BGLs in the both CR-MN and GR-MN treated pigs decreased to the normoglycemia after 2 h (FIGS. 6B and 6C). After the afternoon meal, the CR-MN treated pig immediately increased to a hyperglycemic state. However, BGLs in pig treated with GR-MN showed a small increase and quickly return to normal glycemic state after the mealtime. The BGLs can be maintained at a reduced state overnight until the next meal on the second day. Although the BGLs did decrease to below 40 mg/dL (lower limit of detection of the CGMS) during the administration, no symptom of hypoglycemia was observed since minipigs have lower normal blood glucose ranges (40-80 mg/dL in pigs vs. 80-120 mg/dL in humans).

Figure 7:
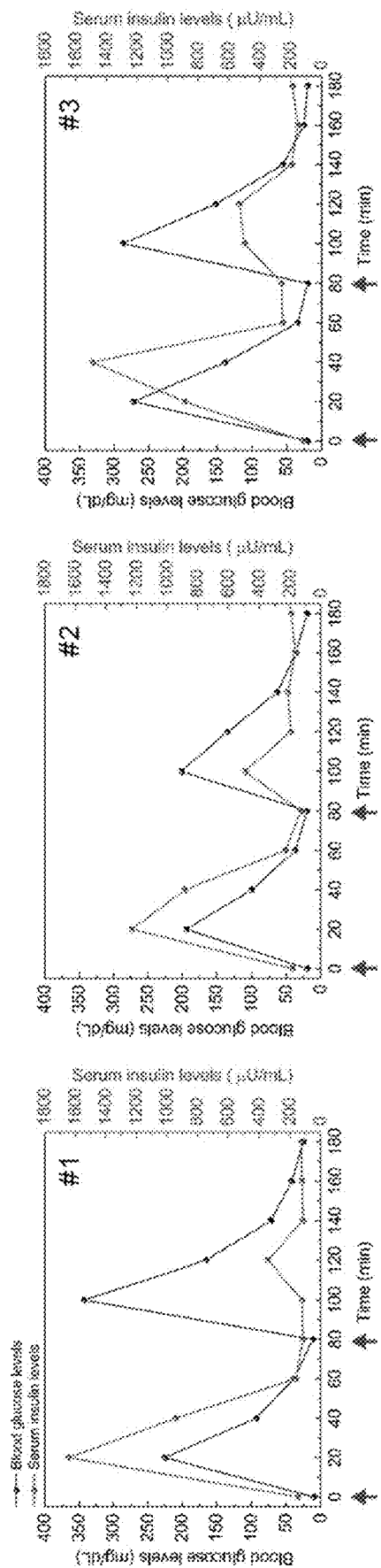
FIG. 7 shows the in vivo glucose-responsive insulin release promoted by intravenous glucose challenge at 4 h post-administration of GR-MN for multiple rounds in three individual experiments. Glucose dose for each round: 0.7 g/kg. The red arrows indicate the timepoints of glucose administration.

An oral glucose tolerance test (OGTT) was performed 4 h post-treatment of CR-MN and GR-MN. Similar to results in the mouse model, BGLs quickly increased to a hyperglycemic state after the glucose challenge in the minipig treated with CR-MN (FIGS. 6D and 6E). In contrast, the administered GR-MN was able to inhibit the increase of BGL after the glucose challenge and re-establish normoglycemia after 100 min. An intravenous glucose tolerance test (IVGTT) was conducted to confirm the in vivo glucose-dependent insulin release. As demonstrated in FIG. 6F, the infused dextrose solution led to an immediate increase in BGLs within the first 20 min, which promoted insulin release into the blood that was verified by the ELISA results. During the experiment, it demonstrated that the endogenous pig insulin was negligible by measuring the blood porcine C-peptide levels. In addition, a second IVGTT was performed when the BGL returned to normoglycemia, and it can also lead to an increase in serum insulin levels with the increase of BGLs (FIG. 7), indicating the GR-MN can achieve the continuous glucose-responsiveness. The histological images using H&E staining indicated that limited acute inflammation occurred after MN administration.

Glucagon Delivery

The current system can be also utilized for glucose-responsive glucagon delivery to treat low blood sugar by adjusting the ratio of DMAEA to 3APBA, which required fast release of glucagon under a hypoglycemic condition. When the glucose concentration was lower than PBA concentrations, one glucose molecule can react with two PBA molecules to form his-complexation, leading to the shrinkage of polymeric matrix with a 0:10 ratio of DMAEA to 3APBA. As shown in FIG. 8, the release rate of glucagon was fast under a hypoglycemic state (50 mg/dL), while it was low under normoglycemia (100 mg/dL) and hyperglycemia conditions (200 and 400 mg/dL). Such polymeric matrix can be integrated with microneedle patch using the same method for biomedical application.

Discussion

MN-based transdermal insulin technology has been exploited to achieve continuous, convenient, and painless treatment for people with diabetes. Additional integration of glucose-responsive formulations holds great promise for improved regulation of BGLs. However, one bottleneck for the translation of such insulin patch involves limited loading capacity of insulin for clinical usage. To this end, this smart insulin patch was developed with a whole polymeric matrix consisting of PBA groups as the glucose-responsive moiety, instead of embedding glucose-responsive formulations such as nanoparticles inside. The MN fabrication process based on an in-situ photo-polymerization strategy is facile and efficient while avoiding the use of organic solvent and elevated temperature to maintain the bioactivity of insulin. In vivo studies confirmed that the bioactivity of insulin loaded within the patches can be maintained at room temperature for over 8 weeks.

The ratios of positively-charged units (DMAEA) and negatively-charged units (3APBA) was adjusted to give an optimized product that possessed a remarkable glucose-dependent insulin release profile. In vivo experiments in STZ-induced diabetic mice demonstrated GR-MN patches offered glucose-responsive regulation of BGLs for a prolonged period of time, without the risk of hypoglycemia. The IPGTT results indicated that a glucose challenge can trigger the fast release of insulin by GR-MN. Based on the promising results in the diabetic mouse model, a series of studies were further conducted on diabetic minipigs with CGMS. It was demonstrated that the GR-MN was able to maintain minipig BGLs in a near normal range for over 20 hours under normal feeding conditions. Increased BGLs caused by intravenous infusion of dextrose solution promoted significant insulin release from GR-MN. Furthermore, the repeated IVGTTs showed that GR-MN had the capability to rapidly respond to the changes in BGLs for multiple rounds of glucose challenges.

Since the crosslinked polymeric matrix of GR-MN is nondegradable, the patch can be completely removed from the skin after treatment. Unlike the dissolvable MN, which can raise the safety concerns associated with the foreign body response to deposited needle tip materials, the well-designed GR-MN revealed good biocompatibility with skin tissues. This is the first demonstration of glucose-responsive behavior in a large diabetic animal model with a transdermal device. The GR-MN patch developed in this study also provides a new platform technology for the development of stimuli-responsive transdermal drug delivery systems to treat other diseases in a smart and simple manner.

Materials and Methods

Materials

All chemicals were purchased from Sigma-Aldrich unless otherwise specified and were used as received. Norland Optical Adhesive 81 (NOA 81) was purchased from Norland Products, Inc. 3-(Acrylamido)phenylboronic acid was purchased from Boron Molecular, U.S.A. The deionized water was prepared by a Millipore NanoPure purification system (resistivity higher than 18.2 MΩ cm–1).

Glucose-Responsive Microneedle (GR-MN) and Non-Responsive Crosslinked Microneedle (CR-MN) Preparation.

GR-MN patch was prepared by in-situ polymerization under UV irradiation. Liquid monomers with photoinitiator was first prepared by dissolve 2-(dimethylamino)ethyl acrylate (DMAEA) and 3-(acrylamido)phenylboronic acid (3APBA) at a certain ratio in N-vinylpyrrolidone (NVP) monomer liquid containing ethylene glycol dimethacrylate (EGDMA, 0.5 mol %) as the crosslinker and Irgacure 2959 (1 mol %) as photoinitiator. Afterward, insulin-preloaded monomers (20 wt %) was directly deposited by pipette onto the MN mold surface. Molds were then place under vacuum for 10 min to allow the liquid to fill into the microneedle mold. After removing the excess solution, the mold was placed under a UV lamp (100 W, 365 nm, Blak-Ray, USA) for 20 min at 4° C. to initiate photo-polymerization. Afterwards, the UV-curable base material (NOA 81) was added onto the mold and further cured under UV light for 10 min to form the base of the patch. The resulting patches were carefully separated from the mold and stored in a sealed six well container at room temperature for further study. CR-MN was prepared in a similar process but without adding of DMAEA and 3APBA.

In Vivo Studies Using Type 1 Diabetic Mice.

The in vivo efficacy of glucose-responsive insulin patches for diabetes treatment was evaluated on streptozotocin (STZ)-induced adult diabetic mice (male C57B6, Jackson Lab, U.S.A.). The plasma-equivalent glucose was measured from tail vein blood samples (~3 µL) of mice using the Clarity GL2Plus glucose meter. The patches used for mice had an 11×11 array of microneedles of pyramid shape, with a side of 300 µm at the base and a height of 700 µm. Five mice for each group were selected to be transcutaneously treated with CR-MN, or GR-MN loaded with human recombinant insulin (insulin dose: 0.5 mg per mouse). The glucose levels of each mouse were monitored over time. In order to measure the plasma insulin concentration in vivo, 25 µL of blood sample was drawn from the tail vein of mice at indicated time points. The serum was isolated and stored at –20° C. until assay. The plasma insulin concentration was measured using Human Insulin ELISA kit according to the manufacturer's protocol (Invitrogen, U.S.A.).

Intraperitoneal glucose tolerance test was conducted to confirm the in vivo glucose responsiveness of MNs 4 h post-administration of crosslinked MN and glucose-responsive MN. Briefly, mice were administrated with CR-MN and GR-MN, and then a glucose solution in PBS was intraperitoneally injected into all mice at a dose of 1.5 g/kg. The glucose levels were monitored over time after injection. The glucose tolerance test on healthy mice was used as control. In order to verify the in vivo IPGTT promoted insulin release, a high glucose dose (3 g/kg) was given 4 h post-administration of GR-MN patches. The glucose levels were monitored and 25 µL of blood sample was drawn from the tail vein of mice at indicated time points. The serum was isolated and stored at –20° C. until assay. The plasma insulin concentration was measured using Human Insulin ELISA kit (Mercodia, U.S.A.).

In Vivo Studies Using STZ-Induced Diabetic Minipig.

Three male Gottingen minipigs (Marshall BioResources, U.S.A.) aged 6 months at arrival were used. Diabetes was induced in the minipigs by means of STZ infusion (150 mg/kg). After seven days of recovery, the successful establishment of the type 1 diabetes model was confirmed by monitoring the blood glucose levels using the continuous glucose monitoring system (CGMS, Dexcom, U.S.A.). All minipigs (weight: 25 kg~30 kg) were fasted overnight before administration. The minipig were transcutaneously treated with CR-MN and GR-MN at the leg sites at an insulin dose of 7 mg for each pig. The patches used for minipigs had a 20×20 array of microneedles of pyramid shape, with a side of 400 µm at the base and a height of 900

μm. The blood glucose levels were continuously monitored using CGMS and two meals daily were normally provided during the experiment.

An oral glucose tolerance test was conducted on diabetic pigs to assess the glucose-responsiveness of MN patches. All minipigs were fasted overnight before administration. The minipig were transcutaneously treated with CR-MN and CR-MN at the leg sites at an insulin dose of 7 mg for each pig. Glucose solution was orally administered to the minipigs 4 h post-treatment at a dose of 1 g/kg. The blood glucose levels were continuously monitored using CGMS.

An intravenous glucose tolerance test was further performed to confirm the blood glucose-promoted insulin release from MN. Three diabetic pigs were treated with transcutaneously treated with GR-MN after an overnight fasting. Dextrose solution (5 wt %) was intravenously infused into pigs at a rate of 1 L/h at 4 h post-treatment at a dose of 0.7 g/kg. The blood was collected from jugular vein at indicated time points for measuring blood glucose using the Clarity GL2Plus glucose meter and serum was then separated using Serum Separator Tube (BD). Serum insulin levels were determined using Human Insulin ELISA kit and porcine C-peptide levels were measured using Porcine C-peptide ELISA kit according to the manufacturer's protocol (Mercodia, U.S.A.).

Statistical Analysis.

All results presented are Mean ±s.d. Statistical analysis was performed using Student's t-test. With a p value <0.05, the differences between experimental groups and control groups were considered statistically significant.

Mechanical Strength Test.

The mechanical strength of microneedles (MNs) was measured by pressing MNs against a stainless-steel plate. The initial gauge was set as 2.00 mm between the MNs tips and the stainless-steel plate, with 10.00 N as load cell capacity. The speed of the top stainless-steel plate movement towards the MNs was 0.1 mm/s. The failure force of MNs was recorded when the needle began to buckle.

In Vitro Glucose Binding Study.

The samples were incubated in 1 mL of PBS solution (NaCl, 137 mM; KCl, 2.7 mM; Na2HPO4, 10 mM; KH2PO4, 2 mM; pH 7.4) with various glucose concentrations (50 mg/dL, 100 mg/dL and 400 mg/dL) at 37° C. for 4 h. After removal of the samples, the remained amount of glucose in the solution were measured using a Clarity GL2Plus glucose meter (Clarity Diagnostics, Boca Raton, Florida). The concentration was calibrated using a glucose standard curve.

In Vitro Release Studies.

To evaluate the glucose-responsiveness of the glucose-responsive matrix, the samples were incubated in 1 mL of PBS solution with various glucose concentrations (0 mg/dL, 100 mg/dL and 400 mg/dL) at 37° C. At predetermined time points, 50 μL of the medium was removed and the released amount of insulin was examined using a Coomassie Plus protein assay. The absorbance was detected at 595 nm on the Infinite 200 PRO multimode plate reader (Tecan Group Ltd., Switzerland), and the insulin content was calibrated with an insulin standard curve. To test the ability to adapt to cyclical changes in glucose levels, the sample was first incubated in PBS buffer with 100 mg/dL glucose for 15 min. At that point, the sample was removed and subsequentially incubated in PBS buffer with 400 mg/dL glucose for another 15 min. This cycle was repeated several times. The released insulin was measured using the same method described above.

REFERENCES

A. Matsumoto, M. Tanaka, H. Matsumoto, K. Ochi, Y. Moro-oka, H. Kuwata, H. Yamada, I. Shirakawa, T. Miyazawa, H. Ishii, Synthetic "smart gel" provides glucose-responsive insulin delivery in diabetic mice. *Sci. Adv.* 3, eaaq0723 (2017).

A. Matsumoto, T. Ishii, J. Nishida, H. Matsumoto, K. Kataoka, Y. Miyahara, A synthetic approach toward a self-regulated insulin delivery system. *Angew. Chem. Int. Ed* 51, 2124-2128 (2012).

A. Summerfield, F. Meurens, M. E. Ricklin, The immunology of the porcine skin and its value as a model for human skin. *Mol. Immunol.* 66, 14-21 (2015).

Association, A. D., Standards of medical care in diabetes—2017 abridged for primary care providers. *Clin. Diabetes* 2017, 35 (1), 5-26.

Atkinson, M. A.; Eisenbarth, G. S., Type 1 diabetes: new perspectives on disease pathogenesis and treatment. *Lancet* 2001, 358 (9277), 221-229.

Bratlie, K. M.; York, R. L.; Invernale, M. A.; Langer, R.; Anderson, D. G., Materials for diabetes therapeutics. *Adv Healthc Mater* 2012, 1 (3), 267-84.

Brooks, W. L.; Sumerlin, B. S., Synthesis and applications of boronic acid-containing polymers: From materials to medicine. *Chem. Rev.* 2015, 116 (3), 1375-1397.

Brownlee, M.; Cerami, A., Glycosylated insulin complexed to concanavalin A: biochemical basis for a closed-loop insulin delivery system. *Diabetes* 1983, 32 (6), 499-504.

Chou, D. H.-C.; Webber, M. J.; Tang, B. C.; Lin, A. B.; Thapa, L. S.; Deng, D.; Truong, J. V.; Cortinas, A. B.; Langer, R.; Anderson, D. G., Glucose-responsive insulin activity by covalent modification with aliphatic phenylboronic acid conjugates. *Proc. Natl. Acad. Sci. U.S.A* 2015, 112 (8), 2401-2406.

Fischel-Ghodsian, F.; Brown, L.; Mathiowitz, E.; Brandenburg, D.; Langer, R., Enzymatically controlled drug delivery. *Proc. Natl. Acad. Sci. U.S.A* 1988, 85 (7), 2403-2406.

G. Vancoillie, R. Hoogenboom, Synthesis and polymerization of boronic acid containing monomers. *Polym. Chem.* 7, 5484-5495 (2016).

Gordijo, C. R.; Koulajian, K.; Shuhendler, A. J.; Bonifacio, L. D.; Huang, H. Y.; Chiang, S.; Ozin, G. A.; Giacca, A.; Wu, X. Y., Nanotechnology-enabled closed loop insulin delivery device: In vitro and in vivo evaluation of glucose-regulated insulin release for diabetes control. *Adv. Funct. Mater.* 2011, 21 (1), 73-82.

Gu, Z.; Dang, T. T.; Ma, M.; Tang, B. C.; Cheng, H.; Jiang, S.; Dong, Y.; Zhang, Y.; Anderson, D. G., Glucose-responsive microgels integrated with enzyme nanocapsules for closed-loop insulin delivery. *ACS Nano* 2013, 7 (8), 6758-66.

I. Hisamitsu, K. Kataoka, T. Okano, Y. Sakurai, Glucose-responsive gel from phenylborate polymer and poly (vinyl alcohol): prompt response at physiological pH through the interaction of borate with amino group in the gel. *Pharm. Res.* 14, 289-293 (1997).

Ito, Y.; Casolaro, M.; Kono, K.; Imanishi, Y., An insulin-releasing system that is responsive to glucose. *J. Controlled Release* 1989, 10 (2), 195-203.

J. Kost, K. Leong, R. Langer, Ultrasound-enhanced polymer degradation and release of incorporated substances. *Proc. Natl. Acad Sci. U.S.A* 86, 7663-7666 (1989).

J. Yu, Y. Zhang, A. R. Kahkoska, Z. Gu, Bioresponsive transcutaneous patches. *Curr. Opin. Biotechnol.* 48, 28-32 (2017).

J. Yu, Y. Zhang, H. Bomba, Z. Gu, Stimuli-responsive delivery of therapeutics for diabetes treatment. *Bioeng. Transl. Med.* 1, 323-337 (2016).

K. Kataoka, H. Miyazaki, M. Bunya, T. Okano, Y. Sakurai, Totally synthetic polymer gels responding to external glucose concentration: their preparation and application to on-off regulation of insulin release. *J. Am. Chem. Soc.* 120, 12694-12695 (1998).

K. Podual, F. Doyle Iii, N. Peppas, Preparation and dynamic response of cationic copolymer hydrogels containing glucose oxidase. *Polymer* 41, 3975-3983 (2000).

Lu, Y.; Aimetti, A. A.; Langer, R.; Gu, Z., Bioresponsive materials. *Nat. Rev. Mater.* 2016, 2, 16075.

M. Brownlee, A. Cerami, A glucose-controlled insulin-delivery system: semisynthetic insulin bound to lectin. *Science* 206, 1190-1191 (1979).

M. Larsen, M. Elander, J. Sturis, M. Wilken, R. Carr, B. Rolin, N. Porksen, The conscious Göttingen minipig as a model for studying rapid pulsatile insulin secretion in vivo. *Diabetologia* 45, 1389-1396 (2002).

M. O. Larsen, B. Rolin, Use of the Gdttingen minipig as a model of diabetes, with special focus on type I diabetes research. *ILAR journal* 45, 303-313 (2004).

M. R. Prausnitz, Microneedles for transdermal drug delivery. *Adv. Drug Del. Rev.* 56, 581-587 (2004).

M. R. Prausnitz, R. Langer, Transdermal drug delivery. *Nat. Biotechnol.* 26, 1261 (2008).

M. Swindle, A. Makin, A. Herron, F. Clubb Jr, K. Frazier, Swine as models in biomedical research and toxicology testing. *Vet. Pathol.* 49, 344-356 (2012).

Matsumoto, A.; Yoshida, R.; Kataoka, K., Glucose-responsive polymer gel bearing phenylborate derivative as a glucose-sensing moiety operating at the physiological pH. *Biomacromolecules* 2004, 5 (3), 1038-1045.

Mo, R.; Jiang, T.; Di, J.; Tai, W.; Gu, Z., Emerging micro- and nanotechnology based synthetic approaches for insulin delivery. *Chem. Soc. Rev.* 2014, 43 (10), 3595-3629.

N. A. Bakh, A. B. Cortinas, M. A. Weiss, R. S. Langer, D. G. Anderson, Z. Gu, S. Dutta, M. S. Strano, Glucose-responsive insulin by molecular and physical design. *Nat. Chem.* 9, 937 (2017).

Ohkubo, Y.; Kishikawa, H.; Araki, E.; Miyata, T.; Isami, S.; Motoyoshi, S.; Kojima, Y.; Furuyoshi, N.; Shichiri, M., Intensive insulin therapy prevents the progression of diabetic microvascular complications in Japanese patients with non-insulin-dependent diabetes mellitus: a randomized prospective 6-year study. *Diabetes Res. Clin. Pract.* 1995, 28 (2), 103-117.

Owens, D. R.; Zinman, B.; Bolli, G. B., Insulins today and beyond. *Lancet* 2001, 358 (9283), 739-746.

Peppas, N.; Huang, Y.; Torres-Lugo, M.; Ward, J.; Zhang, J., Physicochemical foundations and structural design of hydrogels in medicine and biology. *Annu. Rev. Biomed. Eng.* 2000, 2 (1), 9-29.

Podual, K.; Doyle, F. J.; Peppas, N. A., Glucose-sensitivity of glucose oxidase-containing cationic copolymer hydrogels having poly (ethylene glycol) grafts. *J. Controlled Release* 2000, 67(1), 9-17.

Q. Wu, L. Wang, H. Yu, J. Wang, Z. Chen, Organization of glucose-responsive systems and their properties. *Chem. Rev.* 111, 7855-7875 (2011).

R. Mo, T. Jiang, J. Di, W. Tai, Z. Gu, Emerging micro-and nanotechnology based synthetic approaches for insulin delivery. *Chem. Soc. Rev.* 43, 3595-3629 (2014).

R. Yang, M. Wu, S. Lin, R. P. Nargund, X. Li, T. Kelly, L. Yan, G. Dai, Y. Qian, Q. Dallas-Yang, A glucose-responsive insulin therapy protects animals against hypoglycemia. *JCI insight* 3, (2018).

S. P. Sullivan, N. Murthy, M. R. Prausnitz, Minimally invasive protein delivery with rapidly dissolving polymer microneedles. *Adv. Mater.* 20, 933-938 (2008).

Shiino, D.; Murata, Y.; Kubo, A.; Kim, Y. J.; Kataoka, K.; Koyama, Y.; Kikuchi, A.; Yokoyama, M.; Sakurai, Y.; Okano, T., Amine containing phenylboronic acid gel for glucose-responsive insulin release under physiological pH. *J. Controlled Release* 1995, 37(3), 269-276.

Stumvoll, M.; Goldstein, B. J.; van Haeften, T. W., Type 2 diabetes: principles of pathogenesis and therapy. *Lancet* 2005, 365 (9467), 1333-1346.

Sullivan, S. P.; Koutsonanos, D. G.; del Pilar Martin, M.; Lee, J. W.; Zamitsyn, V.; Choi, S.-O.; Murthy, N.; Compans, R. W.; Skountzou, I.; Prausnitz, M. R., Dissolving polymer microneedle patches for influenza vaccination. *Nat. Med* 2010, 16 (8), 915.

T. Ye, X. Jiang, W. Xu, M. Zhou, Y. Hu, W. Wu, Tailoring the glucose-responsive volume phase transition behaviour of Ag@ poly (phenylboronic acid) hybrid microgels: from monotonous swelling to monotonous shrinking upon adding glucose at physiological pH. *Polym. Chem.y* 5, 2352-2362 (2014).

V. Ravaine, C. Ancla, B. Catargi, Chemically controlled closed-loop insulin delivery. *J. Controlled Release* 132, 2-11 (2008).

Veiseh, O.; Tang, B. C.; Whitehead, K. A.; Anderson, D. G.; Langer, R., Managing diabetes with nanomedicine: challenges and opportunities. *Nat. Rev. Drug Discov.* 2015, 14 (1), 45-57.

W. Wu, N. Mitra, E. C. Yan, S. Zhou, Multifunctional hybrid nanogel for integration of optical glucose sensing and self-regulated insulin release at physiological pH. *ACS Nano* 4, 4831-4839 (2010).

Wang, C.; Ye, Y.; Sun, W.; Yu, J.; Wang, J.; Lawrence, D. S.; Buse, J. B.; Gu, Z., Red Blood Cells for Glucose-Responsive Insulin Delivery. *Adv. Mater.* 2017, 29 (18).

X. Wu, Z. Li, X.-X. Chen, J. S. Fossey, T. D. James, Y.-B. Jiang, Selective sensing of saccharides using simple boronic acids and their aggregates. *Chem. Soc. Rev.* 42, 8032-8048 (2013).

Y. Zhang, J. Yu, A. R. Kahkoska, J. Wang, J. B. Buse, Z. Gu, Advances in transdermal insulin delivery. *Adv. Drug Del. Rev.*, (2018).

Yu, J.; Qian, C.; Zhang, Y.; Cui, Z.; Zhu, Y.; Shen, Q.; Ligler, F. S.; Buse, J. B.; Gu, Z., Hypoxia and H2O2 dual-sensitive vesicles for enhanced glucose-responsive insulin delivery. *Nano Lett.* 2017, 17 (2), 733-739.

Yu, J.; Zhang, Y.; Ye, Y.; DiSanto, R.; Sun, W.; Ranson, D.; Ligler, F. S.; Buse, J. B.; Gu, Z., Microneedle-array patches loaded with hypoxia-sensitive vesicles provide fast glucose-responsive insulin delivery. *Proc. Natl. Acad Sci. U.S.A* 2015, 112 (27), 8260-5.

Z. Ding, Y. Guan, Y. Zhang, X. Zhu, Layer-by-layer multilayer films linked with reversible boronate ester bonds with glucose-sensitivity under physiological conditions. *Soft Matt.* 5, 2302-2309(2009).

Z. Gu, A. A. Aimetti, Q. Wang, T. T. Dang, Y. Zhang, O. Veiseh, H. Cheng, R. S. Langer, D. G. Anderson, Injectable nano-network for glucose-mediated insulin delivery. *ACS Nano* 7, 4194-4201 (2013).

What is claimed is:

1. A microneedle patch comprising insulin loaded copolymers; wherein the insulin dissociates from the microneedle in a hyperglycemic environment; wherein the insulin loaded copolymers comprise monomers comprising N-vinylpyrrolidone (NVP), 2-(dimethylamino)ethyl acrylate (DMAEA), and 3-(acrylamido)phenylboronic acid (3APBA).

2. The microneedle patch of claim 1, wherein the insulin loaded copolymers further comprise a crosslinker incorporated into the microneedle that crosslinks the insulin loaded copolymers; and wherein the crosslinker is selected from the group consisting of ethylene glycol, polyvinyl alcohol (PVA), methylacrylate PVA (m-PVA), methylene bisacrylamide, poly(ethylene glycol) diacrylate, and ethylene glycol dimethacrylate (EGDMA).

3. The microneedle patch of claim 2, wherein the crosslinker comprises EGDMA.

4. The microneedle patch of claim 1, wherein the insulin loaded copolymers comprise poly(N-vinylpyrrolidone-co-2-(dimethylamino)ethyl acrylate-co-3-(acrylamido)phenylboronic acid.

5. A self-regulating insulin delivery system comprising the microneedle patch of claim 1.

6. A method of treating hyperglycemia in a subject comprising administering to the subject the microneedle patch of claim 1.

7. The method of claim 6, wherein the hyperglycemia is a symptom of diabetes.

8. A method of treating diabetes in a subject comprising administering to the subject a microneedle patch comprising insulin loaded copolymers; wherein the insulin loaded copolymers comprise N-vinylpyrrolidone (NVP), 2-(dimethylamino)ethyl acrylate (DMAEA), and 3-(acrylamido)phenylboronic acid (3APBA); wherein the insulin loaded copolymers further comprise insulin; and wherein the insulin dissociates from the microneedle in an hyperglycemic environment.

9. The method of claim 8, wherein the insulin loaded copolymers comprise poly(N-vinylpyrrolidone-co-2-(dimethylamino)ethyl acrylate-co-3-(acrylamido)phenylboronic acid.

* * * * *